United States Patent [19]

Avidan et al.

[11] Patent Number: 4,746,761
[45] Date of Patent: * May 24, 1988

[54] PROCESS FOR COVERTING METHANOL TO ALKYL ETHERS

[75] Inventors: Amos A. Avidan, Mantua; Frederick J. Krambeck, Cherry Hill; Samuel A. Tabak, Wenonah, all of N.J.

[73] Assignee: Mobil Oil Corporation, New York, N.Y.

[*] Notice: The portion of the term of this patent subsequent to Aug. 4, 2004 has been disclaimed.

[21] Appl. No.: 65,775

[22] Filed: Jul. 2, 1987

Related U.S. Application Data

[63] Continuation-in-part of Ser. No. 886,996, Jul. 18, 1986, Pat. No. 4,684,757.

[51] Int. Cl.$^4$ ............................ C07C 1/20; C07C 2/00
[52] U.S. Cl. ................................. 585/331; 585/314; 585/315; 585/316; 585/469; 585/640; 585/731
[58] Field of Search ............... 585/314, 315, 316, 331, 585/408, 469, 640, 733, 723, 731

[56] References Cited

U.S. PATENT DOCUMENTS

| | | | |
|---|---|---|---|
| 3,931,349 | 1/1976 | Kuo | 585/640 |
| 3,969,426 | 7/1976 | Owen et al. | 585/640 |
| 3,998,899 | 12/1976 | Daviduk et al. | 585/640 |
| 4,270,929 | 6/1981 | Dang Vu et al. | 585/331 |
| 4,404,414 | 9/1983 | Penick et al. | 585/315 |
| 4,479,018 | 10/1984 | Van Pool | 585/331 |
| 4,506,106 | 3/1985 | Hsia et al. | 585/312 |
| 4,523,046 | 6/1985 | Gould et al. | 585/322 |
| 4,543,435 | 9/1985 | Gould et al. | 585/330 |
| 4,544,777 | 10/1985 | Hutson et al. | 585/331 |
| 4,581,474 | 4/1986 | Hutson et al. | 568/697 |
| 4,628,134 | 12/1986 | Gould et al. | 585/331 |
| 4,628,135 | 12/1986 | Owen et al. | 585/331 |
| 4,684,757 | 8/1987 | Avidan et al. | 585/331 |

Primary Examiner—Asok Pal
Attorney, Agent, or Firm—Alexander J. McKillop; Michael G. Gilman; L. G. Wise

[57] ABSTRACT

A multistage process for producing isoalkyl ethers from lower aliphatic oxygenate feedstock, such as methanol. Feedstock is catalytically converted in a primary catalyst stage at elevated temperature in contact with zeolite catalyst to predominantly $C_2$–$C_7$ lower olefins comprising isobutylene and isoamylene, by-product water and a minor amount of $C_8+$ hydrocarbons, followed by fractionation of the $C_2$–$C_7$ olefins to recover a $C_2$–$C_3$-rich recycle stream for further catalytic conversion in the primary stage. $C_4$–$C_7$ olefins are passed to a second catalytic etherification stage for reaction of isoalkenes with methanol to produce methyl tertiary-butyl ether, methyl isoamylether and higher isoalkyl ethers. The second stage effluent may be fractionated to recover an ether product, $C_5+$ hydrocarbon liquid product, and unreacted butenes. Advantageously, the unreacted butenes are further reacted with isoparaffin in a third catalytic stage under acid catalysis alkylation conditions, and fractionated to recover $C_6+$ alkylate liquid, liquid hydrocarbon product. The ethers may be blended with at least one $C_6+$ hydrocarbon to produce high octane gasoline.

9 Claims, 3 Drawing Sheets

PROCESS FOR COVERTING METHANOL TO ALKYL ETHERS

This application is a continuation-in-part of copending U.S. patent application Ser. No. 886,996, filed July 18, 1986 now U.S. Pat. No. 4,684,751, incorporated herein by reference.

BACKGROUND OF THE INVENTION

This invention relates to an integrated system for converting methanol to high octane liquid fuels, such as hydrocarbons. In particular, it provides a continuous process for producing hydrocarbon fuel products or the like by converting the aliphatic oxygenate feedstock catalytically to an intermediate lower olefinic stream, etherifying $C_4+$ tertiary olefins and alkylating isobutane or other isoparaffins with olefins to produce light distillate and/or gasoline products.

In order to provide an adequate supply of liquid hydrocarbons for use as synfuels or chemical feedstocks, various processes have been developed for converting coal and natural gas to gasoline and distillate. A substantial body of technology has grown to provide oxygenated intermediates, especially methanol. Large scale plants can convert methanol or similar aliphatic oxygenates to liquid fuels, especially gasoline. Demand for liquid hydrocarbons has led to the development of processes for making liquid fuels by various synfuel techniques.

Increasing demand for high octane gasolines blended with lower aliphatic alkyl ethers as octane boosters and supplementary fuels has created a significant demand for isoalkylethers, especially the $C_5$ to $C_7$ methyl alkyl ethers, such as methyl tertiary butyl ether (MTBE) and tertiary amyl methyl ether (TAME). Recently, it has been announced that a commercial plant produces mixed ethers from $C_4$-$C_7$ tertiary olefins and methanol to increase FCC naphtha octane. It has been found advantageous to provide a methanol-based conversion unit which can produce the required intermediate chemicals.

Recent developments in zeolite catalysts and hydrocarbon conversion processes have created interest in utilizing olefins, for producing $C_7+$ alkylate gasoline, etc. In addition to the basic work derived from ZSM-5 type zeolite catalysts, a number of discoveries have contributed to the development of new industrial processes.

The medium pore ZSM-5 type catalysts are useful for converting methanol (MEOH) and other lower aliphatic alcohols or corresponding ethers to lower olefins and also for oligomerizing olefins. Particular interest has been directed to a catalytic process for converting low cost methanol to valuable hydrocarbons rich in ethene and $C_3+$ alkenes. Various processes are described in U.S. Pat. Nos. 3,894,107 (Butter, et al.), 3,928,483 (Chang, et al.), 4,025,571 (Lago), 4,423,274 (Daviduk, et al.), 4,433,189 (Young), and 4,543,435 (Gould and Tabak), incorporated herein by reference. It is generally known that the MTO process can be optimized to produce a major fraction of $C_2$-$C_5$ olefins. Prior process proposals have included a separation section to recover ethene and other light gases from by-product water and heavier hydrocarbons.

It is known that isobutylene may be reacted with methanol over an acidic catalyst to provide methyl tertiary butyl ether (MTBE) and isoamylenes may be reacted with methanol over an acidic catalyst to produce tertiary amyl methyl ether (TAME). The catalyst employed is preferably an ion exchange resin in the hydrogen form. Substantially any acidic catalyst may be employed with varying degrees of success. That is, acidic solid catalysts may be used; such as, sulfonic resins, phosphoric acid modified kieselguhr, silica alumina and acid zeolites.

It has also been recently reported that higher tertiary olefins, typically found in FCC naphtha, may be converted over similar catalysts to mixed ethers. The feed may contain $C_4+$ tertiary olefins, which will produce their respective ethers. A process called "Etherol" has been announced to convert mostly $C_4$-$C_7$ tertiary olefins (C. P. Halsig, B. Schleppinghoff, and D. J. Westlake, "Erdoelchemie and BP Ether Technology—More Scope for Octane Boost" 1986 NPRA Annual Meeting, Mar. 23-25, 1986, Los Angeles, paper AM-86-64). A bifunctional catalyst to hydrogenate diolefins in the feed has also been disclosed (P. M. Lange, F. Martinola and S. Oeckl, "Use Bifunctional Catalysts for MTBE, TAME, and MBK", Hyd. Process. December 1985, 51-52).

SUMMARY OF THE INVENTION

It has been discovered that methanol, DME or the like may be converted to liquid fuels, particulary ethers and alkylates, in a multi-stage continuous process, with integration between the major process units providing an alkylate product stream from olefins and iso-butane produced by primary stage zeolite catalysis. The initial stage MTO process hydrocarbon effluent stream, after by-product water separation and fractionation can be partially fed to an intermediate etherification stage for conversion of $C_4+$ hydrocarbons to MTBE, TAME, or the like, and to a final alkylation stage. Ethene may be recovered by interstage separation for recycle and co-reacted with methanol/DME or other $C_1$-$C_4$ aliphatic oxygenates in the presence of acid zeolite catalyst.

In a preferred embodiment, the invention provides improved a process and integrated continuous technique for converting lower olefins (e.g., propene and butenes) to liquid alkylate hydrocarbons. Propene recovered from the primary stage effluent for balancing $C_3$-$C_4$ olefinic reactants with isobutane in the alkylation stage.

Other objects and features of the invention will be seen in the following description and drawings.

DESCRIPTION OF PREFERRED EMBODIMENTS

Figure 1:
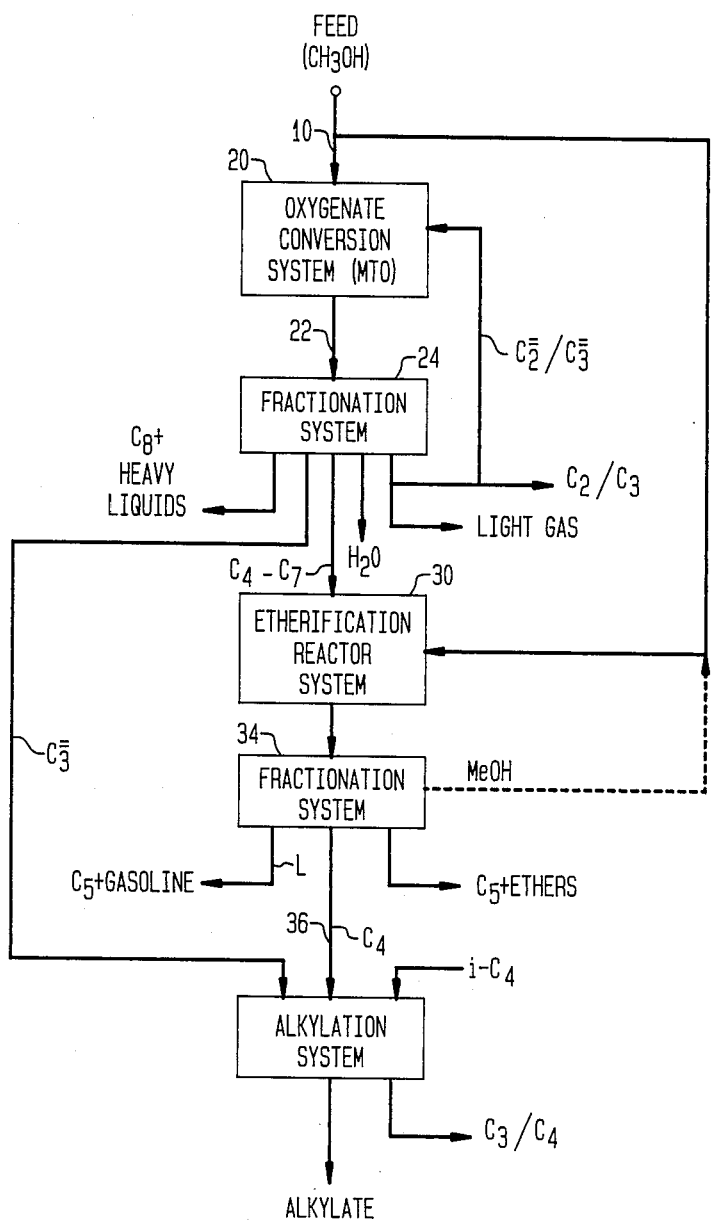
FIG. 1 is a process flow sheet showing the major unit operations and process streams.

Numerous oxygenated organic compounds may be contained in the feedstock material to be converted in the primary stage. Since methanol or its ether derivative (DME) are industrial commodities available from synthesis gas or the like, these materials are utilized in the description herein as preferred starting materials. It is understood by those skilled in the art that MTO-type processes can employ methanol, dimethylether and mixtures thereof, as well as other aliphatic alcohols, ethers, ketones and/or aldehydes. It is known in the art to partially convert oxygenates by dehydration, as in the catalytic reaction of methanol over gamma-alumina to produce DME intermediate. Typically, an equilibrium mixture ($CH_3OH + CH_3OCH_3 + H_2O$) is produced by partial dehydration. This reaction takes place in either conversion of methanol to lower olefins (MTO) or methanol to gasoline (MTG).

Recent developments in zeolite technology have provided a group of medium pore siliceous materials having similar pore geometry. Most prominent among these intermediate pore size zeolites is ZSM-5, which is usually synthesized with Bronsted acid active sites by incorporating a tetrahedrally coordinated metal, such as Al, Ga, or Fe, within the zeolytic framework. These medium pore zeolites are favored for acid catalysis; however, the advantages of ZSM-5 structures may be utilized by employing highly siliceous materials or cystalline metallosilicate having one or more tetrahedral species having varying degrees of acidity. ZSM-5 crystalline structure is readily recognized by its X-ray diffraction pattern, which is characterized by strong lines at d(A): 11.1, 10.0, 3.84, and 3.72. The complete X-ray pattern and synthesis is described in U.S. Pat. No. 3,702,866 (Argauer, et al.), incorporated by reference.

The zeolite catalysts preferred for use herein include the crystalline aluminosilicate zeolites having a silica-to-alumina ratio of at least 12, a constraint index of about 1 to 12 and acid cracking activity (alpha) of about 1–50. Representative of the ZSM-5 type zeolites are ZSM-5, ZSM-11, ZSM-12, ZSM-22, ZSM-23, ZSM-35, ZSM-38, ZSM-45 and ZSM-50. ZSM-5 is disclosed and claimed in U.S. Pat. No. 3,702,886 and U.S. Pat. No. Re. 29,948; ZSM-11 is disclosed and claimed in U.S. Pat. No. 3,709,979. Also, see U.S. Pat. No. 3,832,449 for ZSM-12; U.S. Pat. No. 4,076,979. Also, see U.S. Pat. No. 3,832,449 for ZSM-12; U.S. Pat. No. 4,076,842 for ZSM-23; U.S. Pat. No. 4,016,245 for ZSM-35 and U.S. Pat. No. 4,046,839 for ZSM-38. The disclosures of these patents are incorporated herein by reference. A suitable catalyst for oxgenate conversion is HZSM-5 zeolite with alumina and/or silica binder. Certain of these medium pore shape selective catalysts are sometimes known as porotectosilicates or "pentasil" catalysts. ZSM-5 type catalysts are particularly advantageous because the same material may be employed for dehydration of methanol to DME, conversion to lower olefins and recycle ethylene conversion.

Other catalysts and processes suitable for converting methanol/DME to lower olefins are disclosed in U.S. Pat. No. 4,393,265 (Bonifaz), U.S. Pat. No. 4,387,263 (Vogt, et al.) and European Patent Application 0081683 (Marosi, et al.). In addition to the preferred aluminosilicates, the borosilicate, ferrosilicate silica alumino phosphate (SAPO) and "silicalite" materials may be employed. While small pore (less than 5A) zeolites, such as erionite, offretite, ZSM-34, etc., may be employed for olefin production, they often yield a large amount of ethene. Larger pore (e.g. greater than 7A) zeolites, such as mordenite, X, Y, etc., tend to produce excessive coked deposits. ZSM-5 type catalysts are particularly advantageous because the same material may be employed for dehydration of methanol to DME, conversion to lower olefins and recycle ethylene conversion.

Primary Stage Operation

In this description, metric units and parts by weight are employed unless otherwise stated. Various reactor configurations may be used, including fluidized bed catalytic reactors, moving bed and fixed bed reactors.

The MTO process may be optimized by employing fluid bed primary stage conditions in the temperature range of about 425° C. to 550° C., a pressure range of about 100 to 800 kPa and weight hourly space velocity range of about 0.5 to 3.0 based on ZSM-5 equivalent catalyst and methanol equivalent in the primary stage feedstock. Suitable equipment and operating conditions are described in U.S. Pat. No. 4,579,999 (Gould and Tabak), incorporated herein by reference.

The process is depicted in FIG. 1, wherein methanol-rich oxygenate is fed via conduit 10 to the oxygenate conversion system 20 in the primary stage and the primary stage effluent stream 22 is separated in a primary fractionation system 24 to recover heavy liquid, by-product water, ethene-rich $C_2$–$C_3$ light gas and $C_4$–$C_7$ hydrocarbons, rich in butene and pentene isomers. The major amount of $C_4$–$C_7$ olefins is fed to the etherification reactor system 30 for upgrading to mixed ethers. The ether products may be recovered separately via second fractionation system 34, or may be blended with the $C_8$+ gasoline stream.

The $C_4$ hydrocarbon stream from the secondary ether fractionation system may contain unconverted butylenes ($C_4$=) and isobutane(i-$C_4$); however, the relative amounts of these components are not usually in stoichiometric balance for alkylation. Accordingly, a stream of isobutane is passed through the reactor system. Optionally, propene may be passed from the primary stage to alkylation. Thus, the alkylation reactor system receives unreacted butylenes, mainly 1-butene and/or 2-butene to alkylate isoparaffin derived from the reactor system or brought in to the system.

Figure 2:
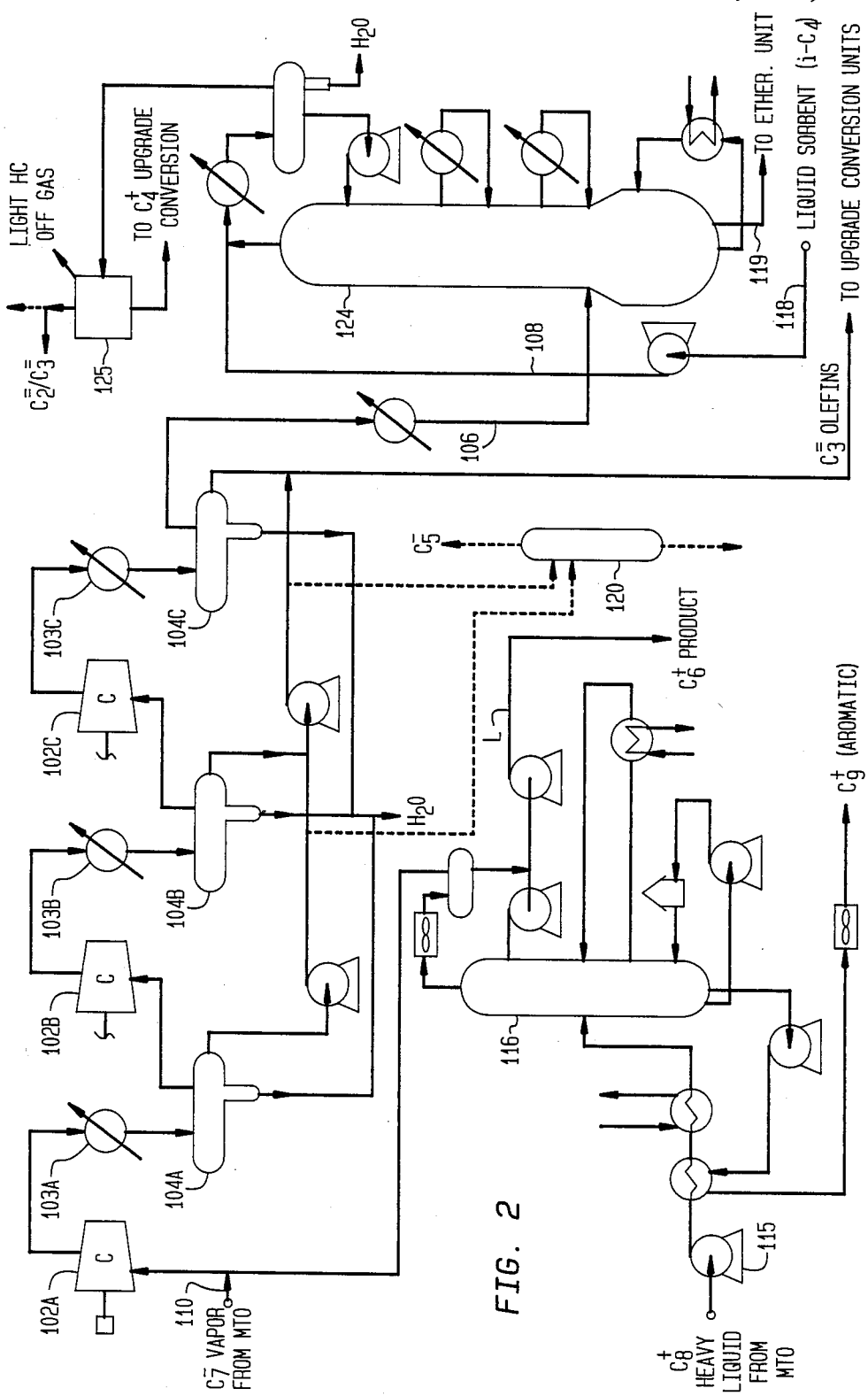
FIG. 2 is a schematic representation of a preferred inter-stage separation system.

In a preferred embodiment depicted in FIG. 2, the primary stage effluent is prefractionated before being sent to olefin upgrading units. Advantageously, the MTO effluent is received at about atmospheric pressure (e.g., 100–150 kPa) and compressed in plural stages to a pressure of about 1500–3000 kPa and separated at about ambient temperature (20°–80° C.). Olefinic liquids rich in $C_4$+ aliphatics may be recovered from the final compressor stage and passed with the $C_8$+ liquid hydrocarbon stream 1 to fractionation tower 124 where $C_4$–$C_7$ alkenes are recovered. Isobutane may be optionally recycled from the alkylation stage as sorbent, as disclosed in U.S. Pat. No. 4,634,798 (Owen et al). A major portion of $C_4$–$C_7$ olefins may be sent to etherification from absorber 124. Referring to the process diagram of FIG. 2, a gaseous feedstream 110 from an MTO reactor is compressed adiabatically in a series of compressors 102A, B, C and passed through corresponding coolers 103A, B, C and phase separators 104A, B, C to recover by-product water and condensed hydrocarbons containing various amounts of $C_3$–$C_7$ aliphatics. A lower olefin intermediate stream 106 is contacted with a liquid sorbent stream 108 in a countercurrent sorption tower 124. Overhead vapor from tower 124 may be further purified in cryogenic separation unit 125 to remove light hydrocarbon gas and $C_4$+ components. The purified ethene and propene may be recovered or recycled to the primary stage MTO reactor for further conversion. The $C_4$–$C_5$ stream from unit 125 is rich in $C_4$–$C_7$ isoalkenes, which may be upgraded to corresponding methyl ethers by passing the etherification reactor 30.

Heavy liquid rich in $C_8$+ hydrocarbons separated from the MTO process primary effluent, is pressurized by pump 115 and fractionated in tower 116 to recover a $C_9^+$ aromatic-rich stream. The condensed overhead, rich in $C_8^+$ aliphatic and aromatic components, may be recovered as product. Liquid sorbent (e.g., $C_8$–$C_9$ hydrocarbons) from line 118 is fed via line 108 to absorber unit 124. $C_4^+$ components sorbed from the feed are removed from column 124 as olefinic sorbate 119, which is feed, with or without fractionation, to the etherification reactor 30 for conversion to MTBE and TAME and higher ethers.

As shown by dashed line, an optional depentanizer tower 120 may be employed to recover $C_5^+$ components condensed from the compressor section. The $C_5^-$ overhead from tower 120 may be fed to the etherification reactor system for upgrading.

Figure 3:
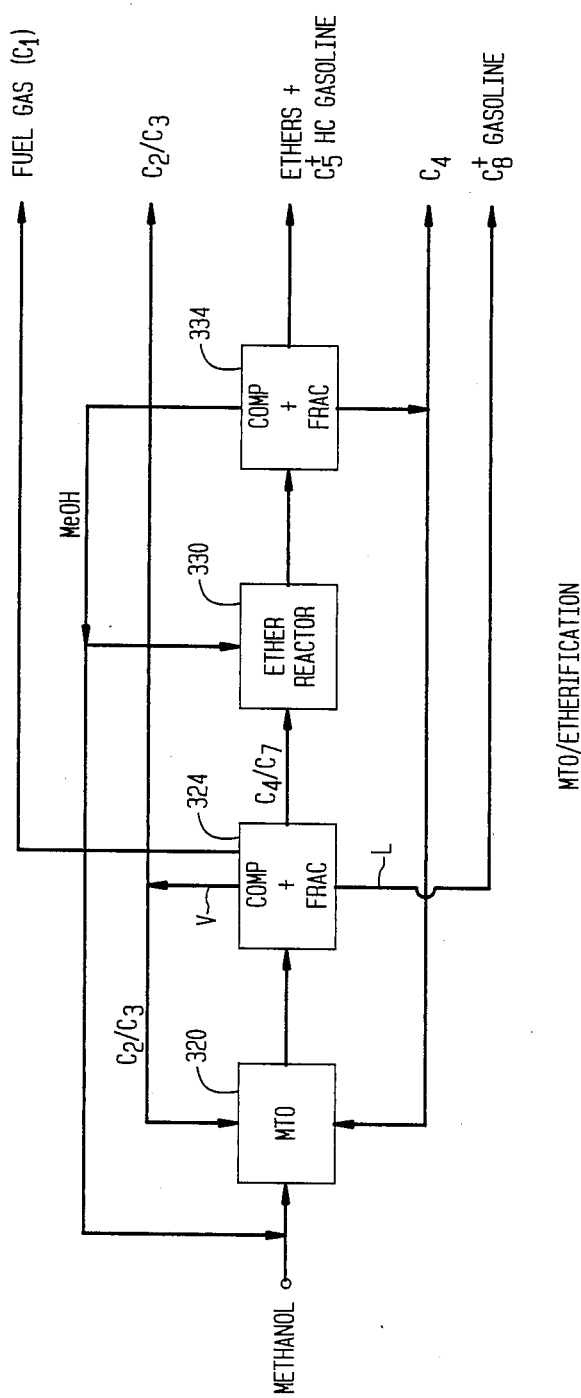
FIG. 3 is an alternative process flow sheet.

In the embodiment of FIG. 3, methanol feedstock is converted in MTO unit 320, compressed and passed to fractionation 324 to provide a $C_8^+$ heavy liquid stream L. The light hydrocarbon vapor stream V is rich in ethene and/or propane separated from the primary stage effluent. The $C_4$–$C_7$ olefinic stream is etherified in reactor 330 and reaction effluent is fractionated to recover recycle methanol, $C_5^+$/blended product and a $C_4$ stream containing unreacted butenes, a portion of which is recylced for further conversion in MTO reactor 320, where the isoalkenes are produced.

The reaction of methanol with isobutylene and isoamylenes, and higher tertiary olefins at moderate conditions with a resin catalyst is known technology, as provided by R. W. Reynolds, et al., *The Oil and Gas Journal*, June 16, 1975, and S. Pecci and T. Floris, *Hydrocarbon Processing*, December 1977. An article entitled "MTBE and TAME—A Good Octane Boosting Combo", by J. D. Chase, et al., *The Oil and Gas Journal*, Apr. 9, 1979, pages 149–152, discusses the technology. The preferred catalyst is Amberlyst 15 sulfonic acid resin.

The ether product of reactor 330 comprising high octane ethers, unreacted olefins and methanol are fractionated in separation zone 334, maintained at a desired pressure, normally atmopsheric pressure, and a temperature within the range of 80° to 125° F., depending on the separation desired. In one embodiment, $C_5$ and lower boiling unreacted olefins are separated along with unreacted methanol are separated and withdrawn for recycle. Unconverted methanol and recycled olefins may be converted in the MTO reactor desired olefin product. Unreacted $C_5^+$ olefins may also be separated from the high octane ethers and blended in pool gasoline. Thus, depending on the separating temperature and pressure conditions relied upon, the high octane ether product separated in zone either with or without $C_5$ plus olefins may be withdrawn as a primary product of the combination process.

MTBE and TAME are known to be high octane ethers. The article by J. D. Chase, et al., *Oil and Gas Journal*, Apr. 9, 1979, discusses the advantages one can achieve by using these materials to enhance gasoline octane. Where a shortage of isobutylene and isoamylene exists and oxygenates are plentiful, the processing combination of the present invention contributes to improved octane gasoline product. The octane blending number of MTBE when 10% is added to a base fuel (R+O=91) is about 120. For a fuel with a low motor rating (M+O=83) octane, the blending value of MTBE at the 10% level is about 103. On the other hand, for an (R+O) of 95 octane fuel, the blending value of 10% MTBE is about 114, and for an (M+O) of 84 octane, the 10% blending value is about 100.

The alkylation process empolyed herein is a well known industrial technique for reacting alkenes with tertiary alkanes (isoparaffins), such as isobutane, isopentane, isohexane, etc. The resulting product is a $C_7^+$ branched chain paraffinic material useful as aviation gasoline, jet fuel or the like. The alkylation of paraffins can be carried out either thermally or catalytically; however, acid catalyst is preferred. Thermal or noncatalytic alkylation of a paraffin with an olefin is carried out at high temperatures (about 500° C.) and pressures 21–41 MPa (3000–6000 psi). Under these conditions, both normal and isoparaffins can be brought into reaction by a free-radical mechanism. Thermal alkylation is not known to be practiced commercially.

The olefin-producing MTO process may simultaneously generate isobutane, but the amount may be insufficient to alkylate the coproduced olefins. A suitable outside source of isobutane is natural gas or a byproduct of methanol-to-gasoline (MTG) processes.

Suitable alkylation processes are described in U.S. Pat. Nos. 3,879,489 (Yurchak et al), 4,115,471 (Kesler), 4,377,721 (Chester) and in the *Kirk-Othmer Encyclopedia of Chemical Technology*, Vol. 2, pp. 50–58 (3rd Ed., 1978) John Wiley & Sons, incorporated herein by reference.

The combined processes are an effective means for converting oxygenated organic compounds, such as methanol, DME, lower aliphatic ketones, aldehydes, esters, etc., to valuable hydrocarbon products. Thermal integration is achieved by employing heat exchangers between various process streams, towers, absorbers, etc.

Various modifications can be made to the system, especially in the choice of equipment and non-critical processing steps. While the invention has been described by specific examples, there is no intent to limit the inventive concept as set forth in the following claims.

What is claimed is:

1. A process for converting oxygenate feedstock comprising methanol to liquid hydrocarbons comprising the steps of
   (a) contacting the feedstock with zeolite catalyst in a primary catalyst stage at elevated temperature and moderate pressure to convert feedstock to hydrocarbons comprising $C_2$–$C_7$ olefins and $C_8^+$ liquid hydrocarbons;
   (b) cooling and separating the primary stage effluent to recover a liquid $C_8^+$ hydrocarbon stream and a light hydrocarbon stream rich in $C_2$–$C_7$ olefins including propylene and $C_4$–$C_7$ isoalkenes;
   (c) compressing at least a portion of the olefinic light hydrocarbon stream to condense a liquid olefinic hydrocarbon stream rich in $C_4$–$C_7$ isoalkenes and recovering a gaseous stream rich in ethene and propene;
   (d) reacting the isoalkenes with methanol in a secondary stage etherification zone by contacting the isoalkenes and methanol with an acid etherification catalyst to produce $C_5$–$C_8$ methyl isoalkylethers;
   (e) fractionating the secondary stage effluent to obtain a liquid ether and $C_5^+$ hydrocarbon stream and an olefinic $C_4$ stream rich in unreacted butenes and isobutane;
   (f) reacting the butene-rich olefinic stream from step (e) with isobutane in a catalytic alkylation stage in contact with acid alkylation catalyst to convert at least a portion of olefins to alkylate gasoline; and (g) recycling ethene and/or propene in a gaseous stream to the primary catalytic stage.

2. The process of claim 1 wherein primary stage feedstock is converted over HZSM-5 catalyst to provide a light olefinic hydrocarbon vapor stream comprising a major amount of $C_3$–$C_7$ olefins and a minor amount of ethene.

3. The process of claim 1 further comprising the step of compressing and fractionating gaseous effluent separated from primary stage effluent to recover a recycle gas stream containing at least 90% of ethene from the primary catalytic stage.

4. The process of claim 1 wherein the primary stage catalyst comprises ZSM-5 type zeolite and ethene is recycled to the primary stage at a rate of about 1 to 10 parts ethene per 100 parts by weight of methanol equivalent in the feedstock.

5. The process of claim 1 wherein the light hydrocarbon vapor stream separated from the primary stage effluent is compressed in a plurality of compression stges to condense liquid olefinic hydrocarbons, and wherein uncondensed compressed light hydrocarbons are further fractionated to recover a recycle stream containing at least 90 mole percent ethene and propene.

6. The process of claim 1 wherein isobutane is reacted with butene-1 and butene-2 in the alkylation stage in the presence of a liquid phase acid catalyst at a pressure of about 1500 to 3000 kPa.

7. A multistage process for producing high octane fuel from lower aliphatic oxygenate feedstock which comprises the steps of (a) catalytically converting oxygenate feedstock in a primary catalyst stage at elevated temperature in contact with zeolite catalyst to predominantly $C_2$–$C_7$ lower olefins comprising $C_4$–$C_7$ isoalkenes, by-product water and a minor amount of $C_8^+$ hydrocarbons;

(b) fractionating the $C_2$–$C_7$ olefins to recover a $C_2$–$C_3$-rich recycle stream for further catalytic conversion in the primary stage and passing $C_4$–$C_7$ olefins to a second catalytic etherification stage for reaction of $C_4$–$C_7$ isoalkenes with methanol to produce corresponding $C_5$–$C_8$ ethers;

(c) fractionating second stage effluent to recover an ether product, $C_5^+$ hydrocarbon liquid product, isobutane and unreacted n-butenes;

(d) further reacting the unreacted n-butenes with isobutane in a third catalytic stage under acid catalysis alkylation conditions;

(e) recovering $C_7^+$ alkylate liquid hydrocarbon;

(f) recovering propene from step (b) fractionation and reacting said recovered propene with excess isobutane in step (d); and (g) blending the ether with at least one liquid hydrocarbon to produce high octane gasoline.

8. The process of claim 7 wherein substantially the entire product is recovered with $C_5^+$ hydrocarbon liquid as a high octane gasoline stream.

9. The process of claim 7 wherein unreacted methanol from the etherification stage is recovered with $C_5^+$ hydrocarbon liquid product.

* * * * *